(12) United States Patent
Shi et al.

(10) Patent No.: US 11,093,685 B2
(45) Date of Patent: Aug. 17, 2021

(54) ATOM TYPE DEFINITION SYSTEM AND ATOM TYPE MATCHING METHOD THEREOF

(71) Applicant: SHENZHEN JINGTAI TECHNOLOGY CO., LTD., Guangdong (CN)

(72) Inventors: Xuekun Shi, Guangdong (CN); Fenglei Cao, Guangdong (CN); Mingjun Yang, Guangdong (CN); Guangxu Sun, Guangdong (CN); Peiyu Zhang, Guangdong (CN); Jian Ma, Guangdong (CN); Lipeng Lai, Guangdong (CN); Shuhao Wen, Guangdong (CN)

(73) Assignee: SHENZHEN JINGTAI TECHNOLOGY CO., LTD., Guangdong (CN)

( * ) Notice: Subject to any disclaimer, the term of this patent is extended or adjusted under 35 U.S.C. 154(b) by 223 days.

(21) Appl. No.: 16/465,564

(22) PCT Filed: May 4, 2018

(86) PCT No.: PCT/CN2018/085724
§ 371 (c)(1),
(2) Date: May 30, 2019

(87) PCT Pub. No.: WO2019/134315
PCT Pub. Date: Jul. 11, 2019

(65) Prior Publication Data
US 2020/0342159 A1  Oct. 29, 2020

(51) Int. Cl.
*G06F 40/103* (2020.01)
*G16C 10/00* (2019.01)
(Continued)

(52) U.S. Cl.
CPC ........... *G06F 40/103* (2020.01); *G06F 17/16* (2013.01); *G06F 40/151* (2020.01); *G16C 10/00* (2019.02); *G16C 20/80* (2019.02)

(58) Field of Classification Search
CPC ...... G06F 40/103; G06F 40/151; G06F 17/16; G16C 10/00; G16C 20/80
See application file for complete search history.

(56) References Cited

U.S. PATENT DOCUMENTS

2003/0195734 A1* 10/2003 Sun ................. G16C 10/00
703/12

FOREIGN PATENT DOCUMENTS

| CN | 101196963 | 6/2008 |
|---|---|---|
| CN | 102609246 | 7/2012 |
| CN | 102609604 | 7/2012 |

OTHER PUBLICATIONS

"International Search Report (Form PCT/ISA/210) of PCT/CN2018/085724," dated Jan. 30, 2019, pp. 1-5.

* cited by examiner

*Primary Examiner* — Quoc A Tran
(74) *Attorney, Agent, or Firm* — JCIP Global Inc.

(57) ABSTRACT

The invention belongs to the technical field force fields and particularly provides an atom type definition system and an atom type matching method. The atom type definition system includes an atom type visual UI interface, an atom type matching module, an atom type data management module and an atom type format transformation module. The atom type data management module includes an atom type definition data package. The system and method can describe various complicated atomic chemical environments, the description capability is improved, and the computation of a force field can be more accurate. According to the invention, convenient operation on an atom type can be realized, and (Continued)

addition, deletion, modification, inquiry as well as statistics of multiple dimensions are very visual and convenient.

3 Claims, 5 Drawing Sheets

(51) Int. Cl.
*G06F 40/151* (2020.01)
*G06F 17/16* (2006.01)
*G16C 20/80* (2019.01)
*G06F 17/00* (2019.01)

ATOM TYPE DEFINITION SYSTEM AND ATOM TYPE MATCHING METHOD THEREOF

CROSS-REFERENCE TO RELATED APPLICATION

This application is a 371 application of an international PCT application serial no. PCT/CN2018/085724, filed on May 4, 2018, The entirety of the above-mentioned patent application is hereby incorporated by reference herein and made a part of this specification.

BACKGROUND OF THE INVENTION

1. Technical Field

The invention belongs to the technical field of force fields and particularly provides an atom type definition system and an atom type matching method thereof.

2. Description of Related Art

The force field technology is a computing technology used for accurately computing the structure and energy in molecule and crystal simulation. An atom type definition system is a core system of the force field technology. Existing force fields including Amber, CHARMM, OPLS, OpenFF and the like have their own atom type definition systems, and are different in the number of atom types, definition modes of chemical environments around atoms, data formats, usage modes and the like. The quality of an atom type definition system influences the difficulty and cost of force field construction and also directly influences the computation accuracy of force fields in use.

The existing atom type definition systems of the force fields mainly have the following problems.

1. Many atoms of different types are classified into a same type due to the insufficient distinction degree of the atom types on the chemical environments around atoms, and consequentially, the computation accuracy is reduced.

2. An atom type definition method has considerable limitations, it is very difficult to describe chemical environments, such as a loop, a bridge and a nest, through a general definition method based on SMARTS and wildcard characters, and the performance is poor.

3. The atom types are difficult to extend, when the atom types are insufficient and need to be additionally increased, a large amount of manpower and time (generally from 2-3 years to 5-10 years) are consumed each time of upgrading due to the lack of a perfect method or tool for extending.

4. The atom types are difficult to view and edit, and without the assistance from of a friendly visual tool, errors easily occur during viewing and modification.

5. Formation conversion between the atom types is difficult, and the atom types are respectively stored and used as data models of text lines cannot be used in a cross manner or compared easily as expected by users.

BRIEF SUMMARY OF THE INVENTION

Aim at the above technical problem, the invention provides an atom type definition system with higher efficiency and higher matching accuracy, and an atom type definition method thereof.

The specific technical scheme is as follows.

The atom type definition system includes an atom type visual UI interface, an atom type matching module, an atom type data management module and an atom type format transformation module, wherein the atom type data management module includes an atom type definition data package.

The atom type definition data package has an atom type definition mode and contains all definitions of an atom type; the definitions of the atom type include a name and an element of the atom type, a description of a chemical environment around an atom conforming to this atom type as well as a hierarchical dependency relationship of the atom type.

The atom type data management module is a bottom basis of the whole system and supports the addition, modification and deletion of an atom type as well as inquiry and statistics of various dimensions.

The atom type matching module efficiently and accurately matches each atom in a given molecule with the corresponding atom type.

The atom type format transformation module realizes mutual transformation of existing atom types of force fields.

The atom type visual UI interface is connected with the atom type matching module, the atom type data management module and the atom type format transformation module in a communication manner, and the atom type matching module and the atom type format transformation module are respectively connected with the atom type data management module in a communication manner.

An atom type matching method of the atom type definition system includes the following steps.

(1) Select a molecule file with an atom type to be matched on the atom type visual UI interface by a user, transmit the molecule file of the atom type and a format to be transformed to the atom type format transformation module, and then transform a transformed molecule file to the atom type matching module.

(2) Mark all molecular bonds contained in the molecule file one by one according to a standard chemical bond type by the atom type matching module; and connect atoms having molecular bonds and attributes marked into a data structure of a graph.

(3) Perform subgraph matching on a graph of atom types contained in the atom type definition data package as well as the graph.

A matching method includes the following steps: transforming an input molecule containing n atoms into an n*n matrix, wherein in the n*n matrix, a point P (i,j) represents types of edges of the $i^{th}$ atom and the $j^{th}$ atom, 0 represents non-bonding, 1 represents a single bond, 2 represents a double bond, 3 represents triple bonds, 4 represents an aromatic bond, and 5 represents a conjugated bond; amplifying the n*n matrix into an (n+1)*(n) matrix, wherein a value, transformed according to corresponding attribute, of each atom is added to a first column of the (n+1)*(n) matrix, a transformation method is as follows: element number+charge*100+loop edge number*1000+aromaticity*100000+conjugacy*1000000, 0 represents that the aromaticity and the conjugacy do not exist, and 1 represents that the aromaticity and the conjugacy exist; then transforming a graph of atom types into a matrix through the above method; finally combining the graph of atom types according to all equal lengths which are throughout the molecular graph, wherein if each row of an atom type matrix is equally matched in a same manner, the subgraph matching succeeds; or otherwise, the subgraph matching fails.

(4) Add a successfully matched atom type to a matching list of the corresponding atom contained in the molecule by the atom type data management module.

(5) After all atom types are completely matched, find out an atom type with a deepest hierarchy from a matching list of each atom as the atom type of the corresponding atom by the atom type matching module.

(6) Transform the completely matched lists of the atom types and then send the transformed lists to the atom type visual UI interface by the atom type format transformation module, and show type marks on a 2D molecular graph to a user.

The atom type definition system and the atom type definition method of the invention have the following technical effects.

1. The atom type definition mode designed by the invention can describe a nesting relation, a succession relation, a hierarchy relation, a tree-form relation and various complicated atomic chemical environments and has a capability far superior to that of the existing definition method based on SMARTS, which can only describe a single atom type and cannot describe the nesting relation, the succession relation, the hierarchy relation, the tree-form relation or other relations. Due to the improvement on the description capability, richer and more accurate atom types can be described, so that the computation of force fields can be more accurate.

2. The data management module of the invention can conveniently operate an atom type in cooperation with the visual UI interface, and addition, deletion, modification, inquiry as well as statistics of multiple dimensions are visual and convenient. The existing atom type system does not realize the corresponding function, the addition, deletion and modification of a text file can only be manually edited and cannot be interactively operated, an atom type can be checked only by referring to the original definition, which is very obscure and is very poor in readability, in the text file; and the existing atom type system cannot achieve statistics of the existing atom types, so that users cannot have a compressive acquaintance about the atom types. These problems can be solved by the invention, so that the development efficiency of atom types is greatly improved.

3. Compared with the existing method, an atom type algorithm in the invention has higher efficiency and higher matching accuracy.

4. The invention supports the mutual transformation of definitions of existing atom types of force fields and has a higher supporting degree than the existing system and the existing tool.

DETAILED DESCRIPTION OF THE INVENTION

One specific embodiment of the invention is used for a computation and simulation system for pharmaceutical molecule and bioprotein combination. A large amount of computation is demanded in the field of biological and pharmaceutical research and development to simulate the combination condition of different pharmaceutical molecule conformations and bioprotein target spots, so that a most appropriate pharmaceutical molecule conformation is found to be used for subsequent pharmaceutical development. A commercial system capable of completing simulation has been developed in this industry, and a system with similar functions is independently being researched and developed by the invention. The key of this system lies in accurate computation of the combination capability of a pharmaceutical molecule and a bioprotein by means of force fields, while the key for ensuring the accuracy of force fields lies in a set of accurately-defined atom types. Thus, the invention is applied to this system to establish and optimize the definitions of atom types, so as to provide better force fields for computation and simulation.

The technical scheme of this embodiment the invention is embedded into the computation and simulation system for pharmaceutical molecule and bioprotein combination, as a subsystem, so that researchers can very conveniently optimize the existing force fields and very conveniently introduce a new force field, and the efficiency of adjusting and optimizing a kernel force field of the computation and simulation system is greatly optimized.

Figure 1:
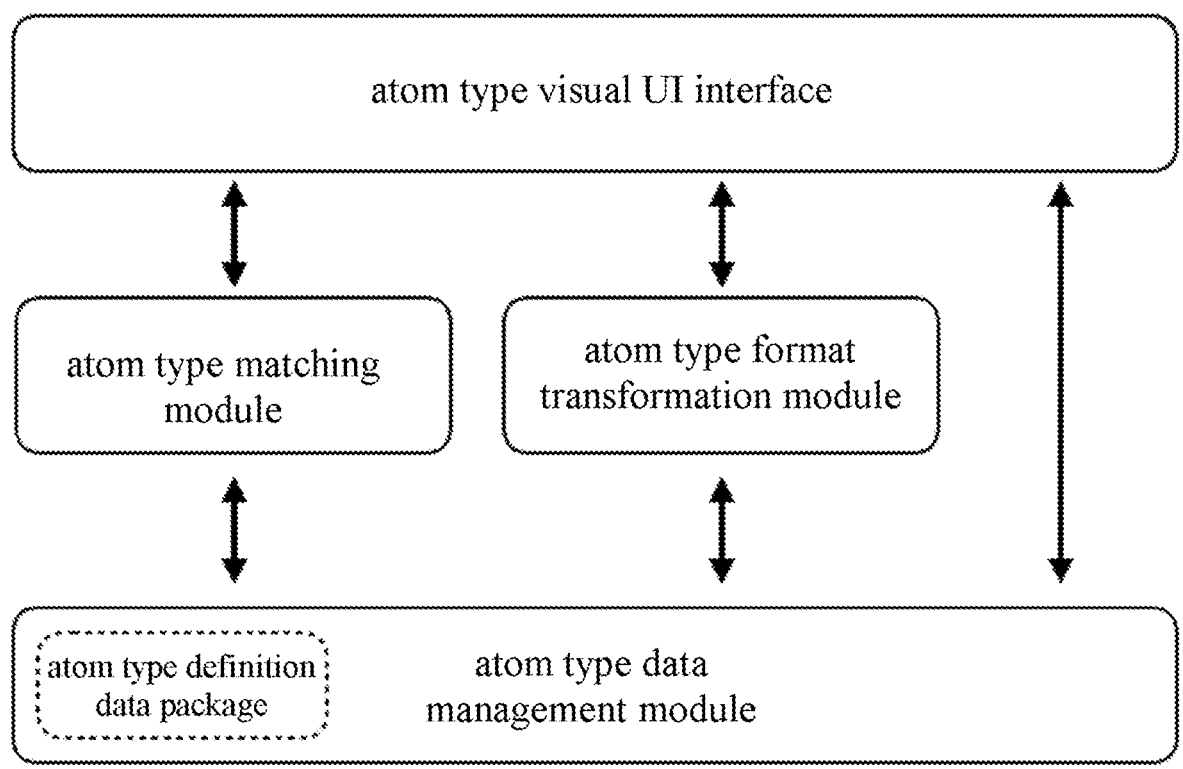
FIG. 1 is a module structure chart of an atom type definition system of the invention.

As shown in FIG. 1, the system includes an atom type definition data package, an atom type data management module, an atom type matching module, an atom type visual UI interface and an atom type format transformation module.

The atom type definition data package has a new atom type definition mode, and particularly, the data package contains all definitions of an atom type. The definitions of the atom type include a name and an element of the atom type, a description of a chemical environment around an atom conforming to this atom type as well as a hierarchical dependency relationship of the atom type; and JSON is adopted as a persistence format of the data package.

Figure 2:
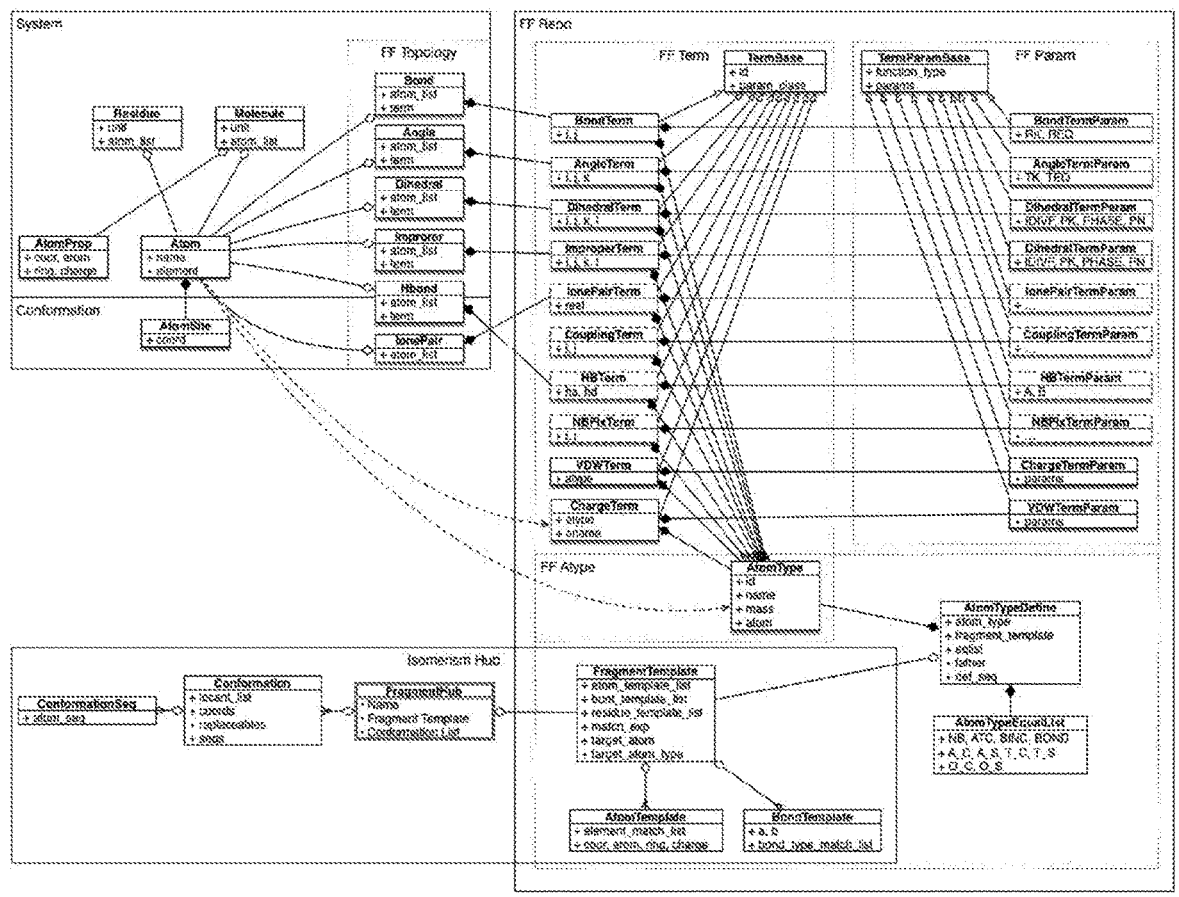
FIG. 2 is a data structure of a data management module of the invention.

As shown in FIG. 2, the atom type data management module is a bottom basis of the whole system and can support the addition, modification and deletion of an atom type as well as inquiry and statistics of various dimensions by adopting an object-oriented modular design.

Figure 3:
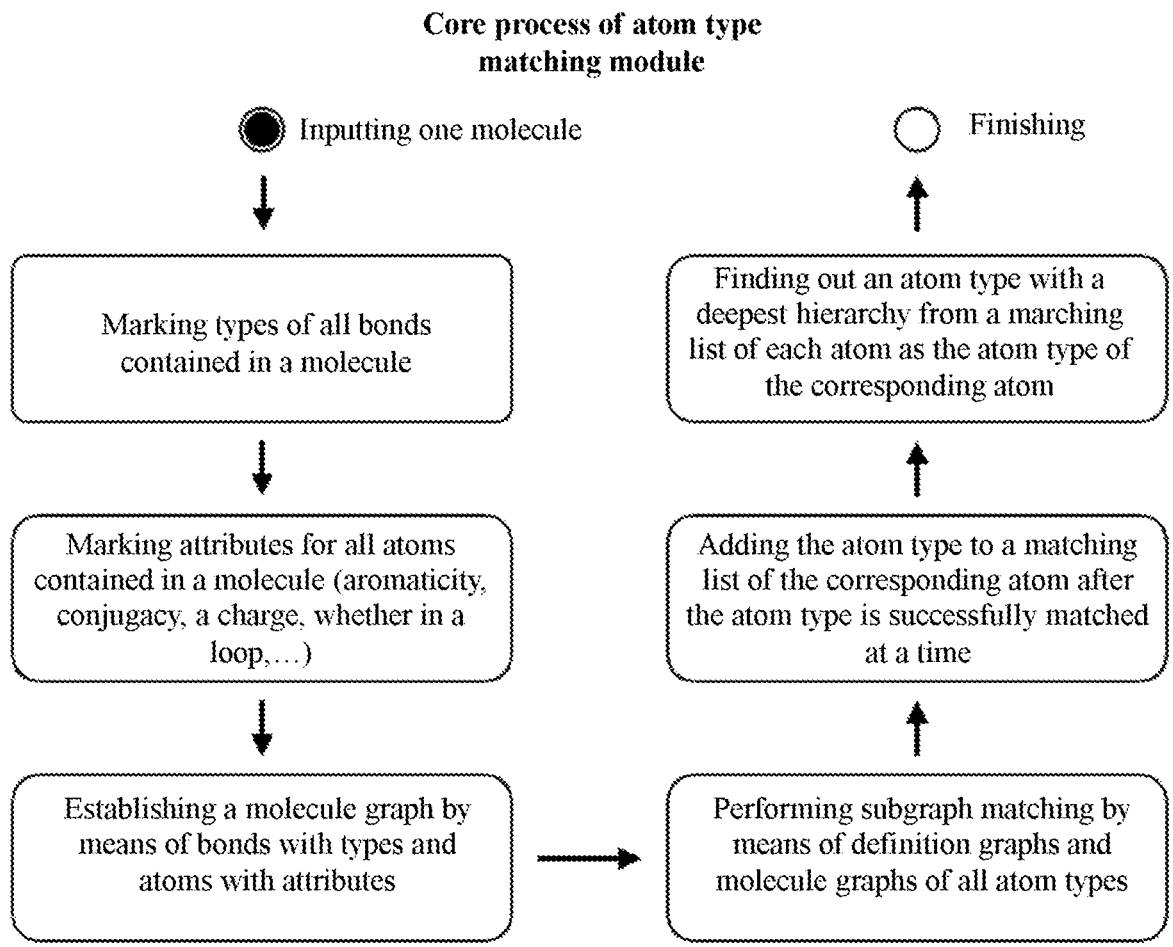
FIG. 3 is an atom type matching process of the invention.

As shown in FIG. 3, the atom type matching module efficiently and accurately matches each atom in a given molecule with the corresponding atom type by dint of the bottom design of a data module.

Figure 4:
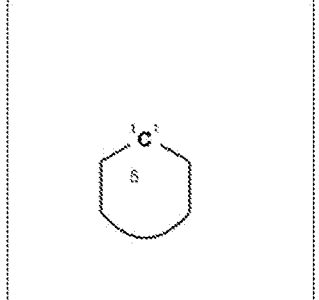
FIG. 4 is an explanation of a visual UI interface of the invention.
Figure 5:
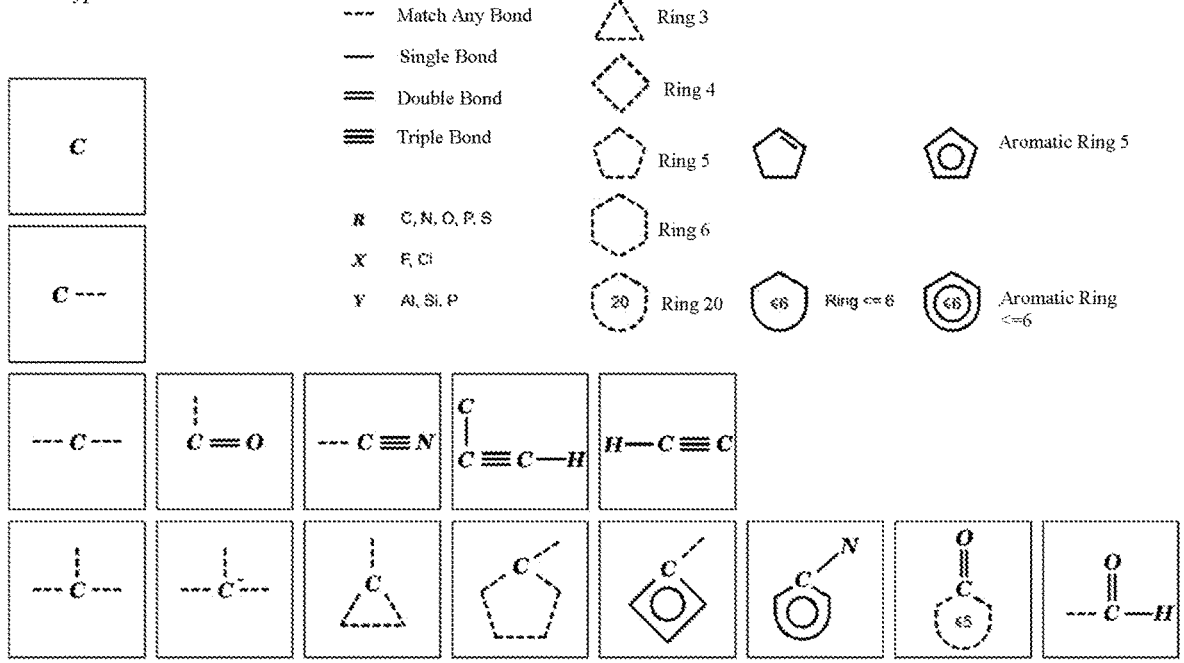
FIG. 5 is 2D visual icons of an atomic chemical environment of the invention.

As shown in FIG. 4, the atom type visual UI interface is used for realizing convenient interaction between users and atom type data. New atomic chemical environment 2D visual icons are designed in the system. This set of icons can visually show the definition of a complicated atomic chemical environment. The atomic chemical environment 2D visual icons are shown in FIG. 5.

Figure 6:
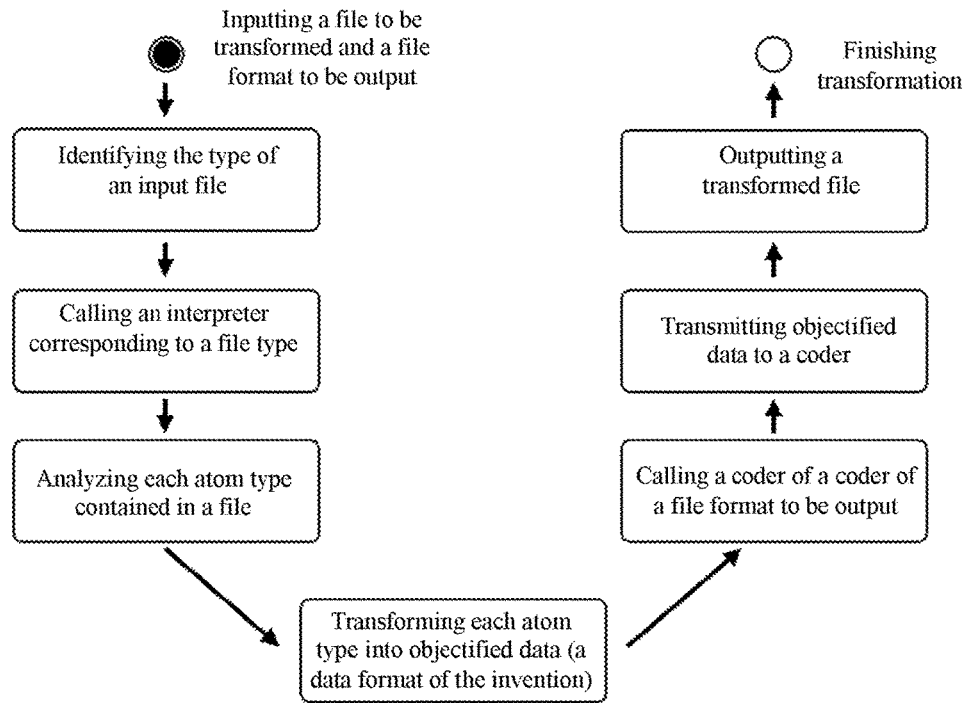
FIG. 6 is a transforming process of a format of an atom type of the invention.

As shown in FIG. 6, the atom type format transformation module supports mutual transformation of all existing atom types of force fields and supports the import and export of various formats.

According to the atom type definition system, the atom type data management module, the atom type matching module and the atom type format transformation module are configured in a microservice frame, the core function of each module is packaged as a module package developed by means of Python, then each module is configured on the microservice frame based on Kubernetes by means of a Flask Webservice frame, and the modules are mutually communicated through an https protocol to provide service support for the outside.

The atom type data management module adopts PostgreSQL as a bottom database. A data control layer logic is packaged also by means of the Flask frame and configured on Kubernetes.

The atom type visual UI interface is developed by means of HTML+CSS+Javascript, adopts a Client/Server frame mode for background services and requests data and transmits a command through the https protocol.

The whole system can be configured on public cloud, a local cluster or a personal computer of a user.

System operation hardware environment: Intel i7 and more advanced processors, a memory more than 16 G and a hard disk memory space more than 500 G.

System operation software environment: Linux4 and more advanced kernel versions, a Python2.7 operation environment.

UI interface service environment: a browser higher than IE8, Chrome and Safari.

A new atom type is established by the invention through the following steps.

(1) The atom type visual UI interface is opened, a right click is performed in a right tree-form navigation control to add a new atom type, at this moment, the system pops up a window to prompt users to input the name of an atom type, and after the name is written, OK is clicked to complete addition; after OK is clicked, the system transmits a current atom type data package ID, the name of the atom type to be newly established and the position of the atom type in tree-form navigation to a microservice of the atom type data management module in a j son format by means of an https protocol, and the data management module inserts these contents into a database to complete addition.

(2) A chemical environment of the atom type is modified and edited and an element, a charge, the number of loop edges, aromaticity, the number of surrounding connected atoms and conjugacy are written on a left atom type detail page. The operation mode of the system is as above.

(3) The position of the atom type on a definition tree can be adjusted by setting a father node and a child node. The operation mode of the system is as above.

The definition of an original atom type is imported by system of the invention through the following steps.

(1) An open button is clicked in the top right corner of the visual UI interface, and a j son file of an atom type is selected from a local file system.

(2) The visual UI interface transmits the j son file selected by a user to the microservice of the data management module, and the data management module analyzes the j son file according to a structure, loads data into a memory according to a data model in FIG. 2 and stores the j son file into a PostgreSQL database.

An atom type of a molecule is matched by the invention through the following step.

(1) An open button is clicked in the top right corner of the visual UI interface, a molecule file with an atom type to be matched is selected from a local file system, wherein xyz, mol, pdb and other molecule files are supported.

(2) The visual UI interface transmits the molecule file to the microservice of the atom type matching module.

(3) The atom type matching module marks all molecular bonds contained in a molecule one by one according to a standard chemical bond type, such as a single bond, a double bond, an aromatic bond and a conjugated bond.

(4) The matching module marks attributes for each atom contained in the molecule, and the attributes include an element, a charge, the number of loop edges, aromaticity, the number of surrounding connected atoms and conjugacy.

(5) The atoms having molecular bond and the attributes marked are connected to obtain a data structure of a graph.

(6) Subgraph matching is performed on a graph of atom types contained in the atom type definition data package as well as a graph of the molecule; a matching method includes the following steps: transforming an input molecule containing n atoms into an n*n matrix, wherein in the n*n matrix, a point P (i,j) represents types of edges of the $i^{th}$ atom and the $j^{th}$ atom, 0 represents non-bonding, 1 represents a single bond, 2 represents a double bond, 3 represents a triple bond, 4 represents an aromatic bond, and 5 represents a conjugated bond; amplifying the n*n matrix into an (n+1)*(n) matrix, wherein a value, transformed according to corresponding attribute, of each atom is added to a first column of the (n+1)*(n) matrix, a transformation method is as follows: element number+charge*100+loop edge number*1000+aromaticity*100000+conjugacy*1000000, 0 represents that the aromaticity and the conjugacy do not exist, and 1 represents that the aromaticity and the conjugacy exist; then transforming the graph of atom types into a matrix through the above method; finally combining the graph of atom types according to all equal lengths which are throughout the molecular graph, wherein if each row of an atom type matrix is equally matched in the same way, subgraph matching succeeds; or otherwise, the subgraph matching fails.

(7) The atom type matching module adds a successfully matched atom type to a matching list of the corresponding atom contained in the molecule.

(8) After all atom types are completely matched, the atom type matching module finds out an atom type with a deepest hierarchy from a matching list of each atom as the atom type of the corresponding atom.

(9) The atom type matching module transmits completely matched atom type lists to the visual UI interface in a j son mode, and type marks are shown on a 2D molecular graph by the visual UI interface to a user.

Wherein, the atom type format is transformed by the invention through the following steps.

(1) An open button is clicked in the top right corner of the atom type visual UI interface, a file to be matched is selected from a local file system, wherein files in data formats of Amber, Gromacs, CHARMM, MacroModel and j son are supported.

(2) The atom type visual UI interface transmits an atom type file and a format to be transformed to the microservice of the atom type format transformation module.

(3) The atom type format transformation module identifies the type of an input file and calls an interpreter of the corresponding file according to the type, wherein the interpreter is an interpretation function of the atom type format transformation module.

(4) The interpreter interprets each atom type in an interpretation file according to an interpretation rule of the corresponding file and stores each atom type in a memory according to a data structure shown in FIG. 2, wherein the memory is assigned to the atom type format transformation module by the system.

(5) The atom type format transformation module calls a coder of a format to be output, and the coder is a coding function of the atom type format transformation module.

(6) The coder calls data contained in the memory in step (4) and codes the data into a file format to be input; and a coded file is transmitted to the atom type visual UI interface by the atom type format transformation module to be used for a user.

SPECIFIC EMBODIMENTS

Embodiment 1

Prediction of the density of a molecule CCCC. Four carbon atoms of the molecule CCCC are connected with different numbers of hydrogen atoms, the carbon at a head part and the carbon at a tail part are respectively connected with three hydrogen atoms, and two carbons in the middle are connected with two hydrogen atoms. The types of these two types of carbons are not distinguished in atom types of the existing force field, and consequentially, when the density is predicted, an error between the density and an experiment value is about 5%. By adopting the invention, two atom types are added to distinguish the carbons connected with the three hydrogen atoms from the carbons connected with the two hydrogen atoms, and an error of the predicted density of a force field can be reduced within 2%, so that the prediction accuracy is greatly improved. Without adopting the invention, the atom types can be added when necessary only by manual modification of personnel who originally define the atom types, so that the efficiency is low, the period is long, and an actual user does not have the autonomy at all.

Embodiment 2

Prediction of vaporization enthalpy of a molecule $C(C=O)N$. in the molecule $C(C=O)N$, a nitrogen atom is defined according to the type of an amine molecule in the existing force field, and in this way, an error between forecast vaporization enthalpy and an experiment value is about 10%. Through analysis, nitrogen contained in this molecule is in an amide group, a new type of a nitrogen atom is added by the invention for distinguishing, a force field is optimized on this basis, and an error of forecast vaporization enthalpy can be less than 5%, so that the accuracy is double improved. Without adopting the invention, the atom types can be added when necessary only by manual modification of personnel who originally define the atom types, so that the efficiency is low, the period is long, and an actual user does not have independence at all.

What is claimed is:

1. An atom type definition system, comprising: a processer, configured to execute the following modules: an atom type visual UI interface, an atom type matching module, an atom type data management module and an atom type format transformation module, wherein the atom type data management module comprises an atom type definition data package;

the atom type definition data package has an atom type definition mode and contains all definitions of an atom type; the definitions of the atom type include a name, an element of the atom type, a description of a chemical environment around an atom conforming to this atom type, and a hierarchical dependency relationship of the atom type;

the atom type data management module is a bottom basis of the whole system and supports addition, modification, deletion of an atom type and inquiry and statistics of various dimensions;

the atom type matching module matches each atom in a given molecule with a corresponding atom type;

the atom type format transformation module realizes mutual transformation of existing atom types of force fields; and the atom type visual UI interface is connected with the atom type matching module, the atom type data management module and the atom type format transformation module in a communication manner, and the atom type matching module and the atom type format transformation module are respectively connected with the atom type data management module in a communication manner.

2. An atom type matching method of an atom type definition system, the atom type definition system comprising: a processer, configured to execute the following modules: an atom type visual UI interface, an atom type matching module, an atom type data management module and an atom type format transformation module, wherein the atom type data management module comprises an atom type definition data package;

the atom type definition data package has an atom type definition mode and contains all definitions of an atom type; the definitions of the atom type include a name, an element of the atom type, a description of a chemical environment around an atom conforming to this atom type, and a hierarchical dependency relationship of the atom type;

the atom type data management module is a bottom basis of the whole system and supports addition, modification, deletion of an atom type and inquiry and statistics of various dimensions;

the atom type matching module matches each atom in a given molecule with a corresponding atom type;

the atom type format transformation module realizes mutual transformation of existing atom types of force fields; and the atom type visual UI interface is connected with the atom type matching module, the atom type data management module and the atom type format transformation module in a communication manner, and the atom type matching module and the atom type format transformation module are respectively connected with the atom type data management module in a communication manner, wherein the method comprises the following steps:

step (1): selecting a molecule file with an atom type to be matched on the atom type visual UI interface by a user, transmitting the molecule file of the atom type and a format to be transformed to the atom type format transformation module, and then transforming a transformed molecule file to the atom type matching module;

step (2): marking all molecular bonds in the molecule file one by one according to a standard chemical bond type by the atom type matching module, and connecting atoms having molecular bonds and attributes marked into a data structure of a graph;

step (3): performing subgraph matching on a graph of atom types contained in the atom type definition data package as well as the graph;

step (4): adding a matched atom type to a matching list of the corresponding atom in the molecule by the atom type data management module;

step (5): after all atom types are matched, finding out an atom type with a deepest hierarchy from a matching list of each said atom as the atom type of the corresponding atom by the atom type matching module;

step (6): transforming the matched lists of the atom types and then sending the transformed lists to the atom type visual UI interface by the atom type format transformation module, and showing type marks on a 2D molecular graph to a user.

3. The atom type matching method of the atom type definition system according to claim 2, wherein the matching method in step (3) comprises the following steps: transforming an input molecule containing n atoms into an n*n matrix, wherein in the n*n matrix, a point P (i,j) represents types of edges of the $i^{th}$ atom and the $j^{th}$ atom, 0 represents non-bonding, 1 represents a single bond, 2 represents a double bond, 3 represents a triple bond, 4 represents an aromatic bond, and 5 represents a conjugated bond; amplifying the n*n matrix into an (n+1)*(n) matrix, wherein a value, transformed according to corresponding attribute, of each said atom is added to a first column of the (n+1)*(n) matrix, a transformation method is as follows: element number+charge*100+loop edge number*1000+aromaticity*100000+conjugacy*1000000, 0 represents that the aromaticity and the conjugacy do not exist, and 1 represents that the aromaticity and the conjugacy exist; then transforming a graph of atom types into a matrix through the method; finally combining the graph of atom types according to all equal lengths which are throughout the molecular graph, wherein if each row of an atom type matrix is equally matched in a same manner, the subgraph matching succeeds; or otherwise, the subgraph matching fails.

* * * * *